US00PP33597P3

(12) United States Plant Patent
Eggleton

(10) Patent No.: US PP33,597 P3
(45) Date of Patent: Nov. 2, 2021

(54) ***ARMERIA* PLANT NAMED 'DREAM CLOUDS'**

(50) Latin Name: *Armeria pseudarmeria*
Varietal Denomination: Dream Clouds

(71) Applicant: PLANTS MANAGEMENT AUSTRALIA, Dodges Ferry (AU)

(72) Inventor: Steven Michael Eggleton, Wonga Park (AU)

(73) Assignee: Plants Management Australia, Dodges Ferry (AU)

( * ) Notice: Subject to any disclaimer, the term of this patent is extended or adjusted under 35 U.S.C. 154(b) by 0 days.

(21) Appl. No.: 17/031,553

(22) Filed: Sep. 24, 2020

(65) Prior Publication Data

US 2021/0100146 P1 Apr. 1, 2021

(51) Int. Cl.
*A01H 5/02* (2018.01)
*A01H 6/00* (2018.01)
*A01H 6/04* (2018.01)

(52) U.S. Cl.
USPC ..... Plt./263.1
CPC ..... *A01H 6/04* (2018.05)

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Armeria* plant named 'Dream Clouds', characterized by its relatively short, upright and uniformly mounded plant habit; narrow leaves; freely flowering habit; medium-sized inflorescences positioned on relatively short peduncles with white-colored flowers; and good garden performance.

2 Drawing Sheets

Figure 1:
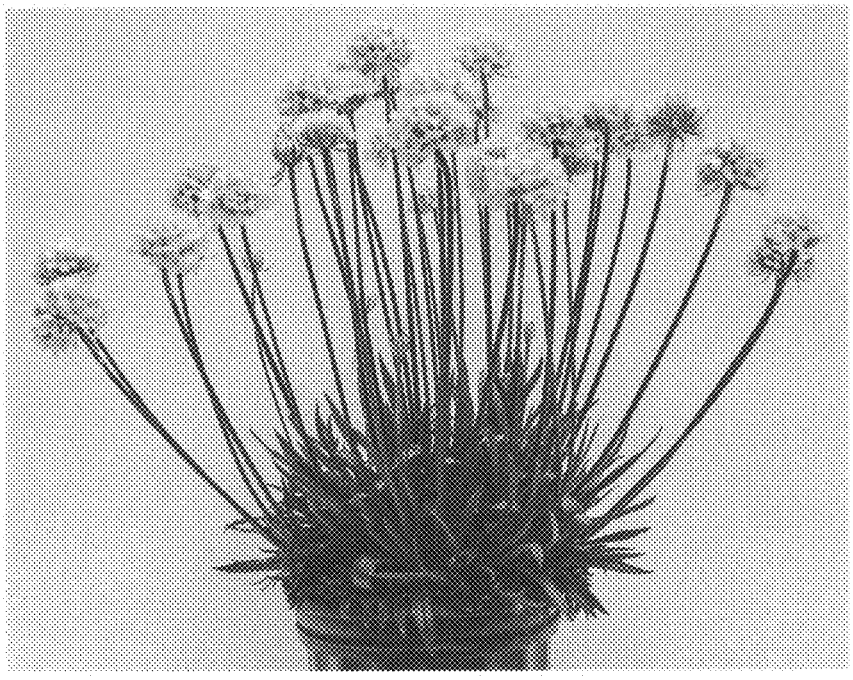

Botanical designation: *Armeria pseudarmeria.*
Cultivar denomination: 'DREAM CLOUDS'.

STATEMENT REGARDING PRIOR DISCLOSURES BY INVENTOR & APPLICANT

An Australia Plant Breeder's Rights application for the instant plant was filed by the Applicant, Plants Management Australia of Wonga Park, Victoria, Australia, on Sep. 26, 2019, application number 2019/207. Foreign priority is claimed to this application and a certified copy of the Australian Plant Breeder's Rights application is filed concurrently with the instant application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date of this application.

BACKGROUND OF THE INVENTION

The present invention relates to a new and distinct cultivar of *Armeria* plant, commonly referred to as Thrift or Sea Pink, botanically known as *Armeria pseudarmeria*, commercially used as a garden plant, and hereinafter referred to by the name 'Dream Clouds'.

The new *Armeria* plant is a product of a planned breeding program in Wonga Park, Victoria, Australia. The objective of the breeding program is to create new *Armeria* plants with uniform upright plant habit, relatively short flowering stems, medium-sized globular inflorescences and good garden performance.

The new *Armeria* plant originated from a cross-pollination conducted by the Inventor in Wonga Park, Victoria, Australia in 2012 of a proprietary selection of *Armeria pseudarmeria* identified as code number IB109-1, not patented, as the female, or seed, parent with *Armeria pseudarmeria* 'Sweet Dreams', disclosed in U.S. Plant Pat. No. 29,612, as the male, or seed, parent. The new *Armeria* plant was discovered and selected by the Inventor as a single flowering plant from within the progeny of the stated cross-pollination grown in a controlled greenhouse environment in Wonga Park, Victoria, Australia in February, 2013.

Asexual reproduction of the new *Armeria* plant since 2014 by vegetative cuttings in a controlled environment in Wonga Park, Victoria, Australia has shown that the unique features of this new *Armeria* plant are stable and reproduced true to type in successive generations.

SUMMARY OF THE INVENTION

Plants of the new *Armeria* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'Dream Clouds'. These characteristics in combination distinguish 'Dream Clouds' as a new and distinct *Armeria* plant:

1. Relatively short, upright and uniformly mounded plant habit.
2. Narrow leaves.
3. Freely flowering habit.

4. Medium-sized inflorescences positioned on relatively short peduncles with white-colored flowers.
5. Good garden performance.

Plants of the new *Armeria* can be compared to plants of the female parent selection. Plants of the new *Armeria* differ primarily from plants of the female parent selection in plant size as plants of the new *Armeria* have shorter peduncles than plants of the female parent selection. In addition, plants of the new *Armeria* have narrower leaves than plants of the female parent selection.

Plants of the new *Armeria* can be compared to plants of the male parent, 'Sweet Dreams'. Plants of the new *Armeria* differ primarily from plants of 'Sweet Dreams' in flower color as plants of the new *Armeria* have white-colored flowers whereas plants of 'Sweet Dreams' have light purple-colored flowers.

Plants of the new *Armeria* can be compared to plants of *Armeria pseudarmeria* 'Daydream', disclosed in U.S. Plant Pat. No. 29,381. Plants of the new *Armeria* differ primarily from plants of 'Daydream' in flower color as plants of the new *Armeria* have white-colored flowers whereas plants of 'Daydream' have medium purplish pink-colored flowers.

Plants of the new *Armeria* can also be compared to plants of *Armeria pseudarmeria* 'Ballerina White', not patented. In side-by-side comparisons, plants of the new *Armeria* differ primarily from plants of 'Ballerina White' in peduncle length and strength as plants of the new *Armeria* have shorter and stronger peduncles than plants of 'Ballerina White'.

BRIEF DESCRIPTION OF THE PHOTOGRAPHS

The accompanying colored photographs illustrate the overall appearance of the new *Armeria* plant showing the colors as true as it is reasonably possible to obtain in colored reproductions of this type. Colors in the photographs may differ slightly from the color values cited in the detailed botanical description which accurately describe the colors of the new *Armeria* plant.

The photograph on the first sheet (FIG. 1) is a side perspective view of a typical flowering plant of 'Dream Clouds' grown in a container.

Figure 2:
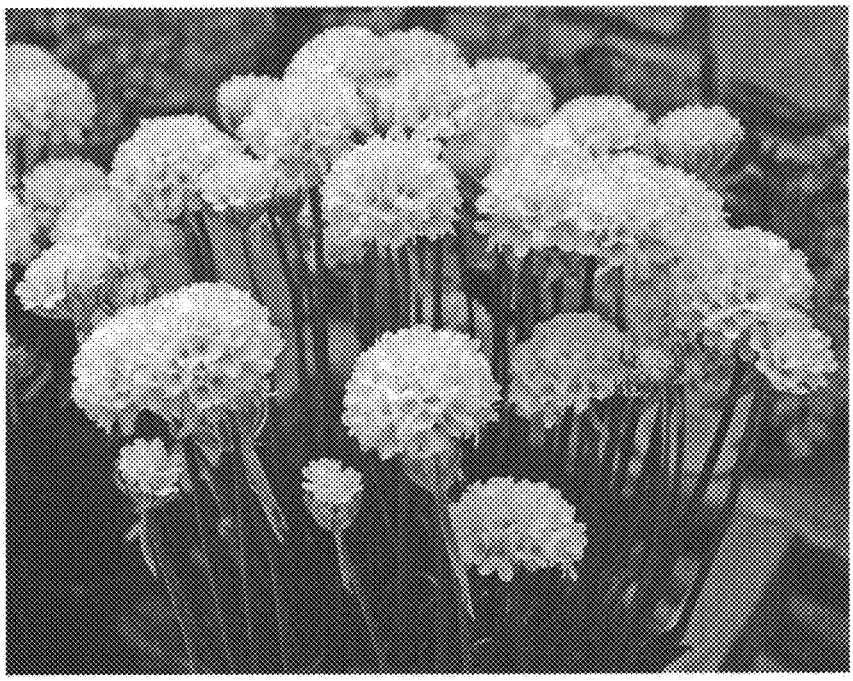

The photograph on the second sheet (FIG. 2) is a close-up view of a typical flowering plant of 'Dream Clouds' grown in a container.

DETAILED BOTANICAL DESCRIPTION

The aforementioned photographs and following observations and measurements describe plants of the new *Armeria* grown during the spring in one-gallon containers in a glass-covered greenhouse in Elburn, Ill. and an outdoor nursery in Fort Worth, Tex. Plants were grown under cultural practices typical of *Armeria* production. During the production of the plants, day temperatures averaged 7° C., night temperatures averaged 2° C. and light levels averaged 3,000 foot-candles. Plants were 26 weeks old when the photographs and description were taken. Color references are made to The Royal Horticultural Society Colour Chart, 2015 Edition, except where general terms of ordinary dictionary significance are used.

Botanical classification: *Armeria pseudarmeria* 'Dream Clouds'.

Parentage:

*Female, or seed, parent.*—Proprietary selection of *Armeria pseudarmeria* identified as code number IB109-1, not patented.

*Male, or pollen, parent.*—*Armeria pseudarmeria* 'Sweet Dreams', disclosed in U.S. Plant Pat. No. 29,612.

Propagation:

*Type.*—By vegetative cuttings.

*Time to initiate roots, summer.*—About ten days at soil temperatures about 20° C. and ambient temperatures about 25° C.

*Time to initiate roots, winter.*—About 20 days at soil temperatures about 20° C. and ambient temperatures about 15° C.

*Time to produce a rooted young plant, summer.*—About 40 days at soil temperatures about 20° C. and ambient temperatures about 25° C.

*Time to produce a rooted young plant, winter.*—About 60 days at soil temperatures about 12° C. and ambient temperatures about 12° C.

*Root description.*—Medium thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a landscape plant; plants relatively compact, upright and uniformly mounded; basally clumping with leaves and flower peduncles developing from the base; freely branching and flowering habit; flowers arranged in dense globular terminal umbels; moderately vigorous growth habit and moderate growth rate.

*Plant height, soil level to top of foliar plane.*—About 17 cm.

*Plant height, soil level to top of inflorescences.*—About 27.5 cm.

*Plant diameter (spread).*—About 26 cm.

Stem description:

*Length.*—About 1 cm.

*Diameter.*—About 5.5 mm.

*Strength.*—Strong.

*Texture and luster.*—Smooth, glabrous; matte.

*Color.*—Close to 175A.

Leaf description:

*Arrangement.*—Basal rosette, simple, sessile.

*Length.*—About 11 cm.

*Width.*—About 6.5 cm.

*Shape.*—Acicular, carinate.

*Apex.*—Acute.

*Base.*—Clasping.

*Margin.*—Entire; not undulate.

*Texture and luster, upper surface.*—Smooth, glabrous; semi-glossy.

*Texture and luster, lower surface.*—Smooth, glabrous; slightly glossy.

*Venation pattern.*—Parallel.

*Color.*—Developing leaves, upper and lower surfaces: Close to between 144A and 146A. Fully expanded leaves, upper surface: Close to between 139A and 147A; towards the base, close to NN155D; venation, close to between 139A and 147A and proximally, close to NN155D. Fully expanded leaves, lower surface: Close to between 139A and 147A; towards the base, close to NN155D; venation, close to 146A and proximally, close to NN155D.

Flower description:

*Flower arrangement and habit.*—Single salverform to star-shaped tubular flowers arranged in dense terminal umbels; flowers sessile; freely flowering habit with about 142 flowers developing per inflorescence and about 48 inflorescences developing per plant during the flowering season; flowers face upright to outwardly depending on position on the inflorescence.

*Fragrance.*—None detected.

*Flowering response.*—Plants begin flowering about 24 weeks after planting and flower continuously in the garden from early spring to early summer.

*Post-production longevity.*—Flowers last about two weeks on the plant; corolla not persistent, calyx persistent.

*Inflorescence height.*—About 2.2 cm.

*Inflorescence diameter.*—About 2.75 cm.

*Flower diameter.*—About 7.5 mm.

*Flower depth (height).*—About 1.1 cm.

*Flower throat diameter.*—About 3 mm.

*Flower tube length.*—About 3.5 mm.

*Flower tube diameter, proximally.*—About 1 mm.

*Flower buds.*—Length: About 1.5 cm. Diameter: About 6 mm. Shape: Ovoid. Texture and luster: Smooth, glabrous; slightly glossy. Color: Close to 144A.

*Petals.*—Quantity and arrangement: Five to six in a single whorl, fused towards the base. Length: About 9 mm. Width: About 3.5 mm to 4 mm. Shape: Elongated spatulate. Apex: Obtuse to broadly acute. Margin: Entire. Texture and luster, upper and lower surfaces: Smooth, glabrous; slightly glossy. Color: When opening, upper and lower surfaces: Close to NN155D; translucent. Fully opened, upper and lower surfaces: Close to NN155D; translucent; color does not change with development.

*Sepals.*—Calyx length: About 8 mm. Calyx diameter, distally: About 4 mm. Calyx diameter, proximally: About 1.5 mm. Calyx shape: Tubular, distally, sepals flaring outwardly. Quantity and arrangement: Five to seven in a single whorl, lower 80% fused. Length: About 8 mm. Width, lobe: About 1.5 mm. Shape, lobe: Roughly deltoid. Apex: Long acuminate. Margin: Entire. Texture and luster, upper and lower surfaces: Smooth, glabrous; papery; matte.

*Involucral bracts.*—Quantity and arrangement: About 14 in a single whorl at the base of the inflorescence. Length: About 1.3 cm. Width: About 3.5 mm. Shape: Roughly deltoid. Apex: Acute. Margin: Entire. Texture and luster, upper and lower surfaces: Smooth, glabrous; matte. Color, upper and lower surfaces: Close to between 144A and 146A.

*Involucral sheath.*—Quantity and arrangement: One at the base of the inflorescence; downwardly orientated. Length: About 1.7 cm to 3.4 cm. Width: About 6 mm. Shape: Roughly rectangular. Apex: Praemorse. Margin: Entire. Texture and luster, upper and lower surfaces: Smooth, glabrous; papery; matte. Color, upper and lower surfaces: Proximally, close to between 144A and 146A and distally, close to NN155D and translucent.

*Peduncles.*—Length: About 21 cm. Diameter: About 3 mm. Aspect: Mostly upright to curving upright. Strength: Strong. Texture and luster: Smooth, glabrous; slightly glossy. Color: Close to 137A.

*Reproductive organs.*—Androecium: Stamen number: Five to seven per flower. Filament length: About 3 mm. Filament color: Close to NN155D. Anther length: About 1 mm. Anther shape: Oblong. Anther color: Close to 9A. Amount of pollen: None observed. Gynoecium: Pistil number: One per flower. Pistil length: About 5 mm, thread-like. Style length: About 4 mm. Style color: Close to NN155D. Stigma diameter: About 0.1 mm. Stigma shape: Pointed. Stigma color: Close to NN155D. Ovary color: Close to 144A.

*Seeds and fruits.*—To date, seed and fruit development have not been observed on plants of the new *Armeria*.

Pathogen & pest resistance: To date, plants of the new *Armeria* have not been observed to be resistant to pathogens and pests common to *Armeria* plants.

Garden performance: Plants of the new *Armeria* have been observed to have good garden performance and to tolerate wind, rain and temperatures ranging from about −29° C. to about 35° C.

It is claimed:

1. A new and distinct *Armeria* plant named 'Dream Clouds' as illustrated and described.

* * * * *